(12) United States Patent
Skelnik et al.

(10) Patent No.: US 9,167,809 B2
(45) Date of Patent: Oct. 27, 2015

(54) CORNEA STORAGE CONTAINER TO MAXIMIZE CORNEA HEALTH

(75) Inventors: Debra Skelnik, Cambridge, MN (US); Roger Wilson, Cambridge, MN (US); John R. Wilson, New Brighton, MN (US)

(73) Assignee: Numedis Incorporated, Isanti, MN (US)

( * ) Notice: Subject to any disclaimer, the term of this patent is extended or adjusted under 35 U.S.C. 154(b) by 1191 days.

(21) Appl. No.: 12/817,982

(22) Filed: Jun. 17, 2010

(65) Prior Publication Data

US 2011/0014690 A1    Jan. 20, 2011

Related U.S. Application Data

(60) Provisional application No. 61/187,919, filed on Jun. 17, 2009.

(51) Int. Cl.
*A01N 1/02* (2006.01)
(52) U.S. Cl.
CPC ............ *A01N 1/0273* (2013.01); *A01N 1/0263* (2013.01)
(58) Field of Classification Search
CPC ..... A01N 1/02; A01N 1/0263; A01N 1/0273; A61F 2/0095; A61F 2/142; A61F 2/1691
USPC .......................................... 435/284.1, 307.1
See application file for complete search history.

(56) References Cited

U.S. PATENT DOCUMENTS

| | | | |
|---|---|---|---|
| 4,695,536 | A | 9/1987 | Lindstrom et al. |
| 4,844,242 | A | 7/1989 | Chen et al. |
| 2008/0294149 | A1 | 11/2008 | Krolman |
| 2011/0008877 | A1 | 1/2011 | Skelnik et al. |

FOREIGN PATENT DOCUMENTS

CN        201243575 Y  *  5/2009

OTHER PUBLICATIONS

English language machine translation of CN201243575 (May 27, 2009), 3 pages.*
File History for U.S. Appl. No. 12/817,978, mailed Jun. 17, 2010. Inventors: Debra Skelnik et al. at www.uspto.gov.

* cited by examiner

*Primary Examiner* — William H Beisner
(74) *Attorney, Agent, or Firm* — Patterson Thuente Pedersen, P.A.

(57) ABSTRACT

An apparatus for shipping, storing, and viewing a cornea comprising a container having a viewing window in a container base, an inner sidewall, and a corneal basket arranged within said container base. The corneal basket is in contact with said inner sidewall and adapted to support a corneoscleral disc by including more than one corneal support rod and more than one disc support surface and a lid that sealingly engages with the container.

12 Claims, 17 Drawing Sheets

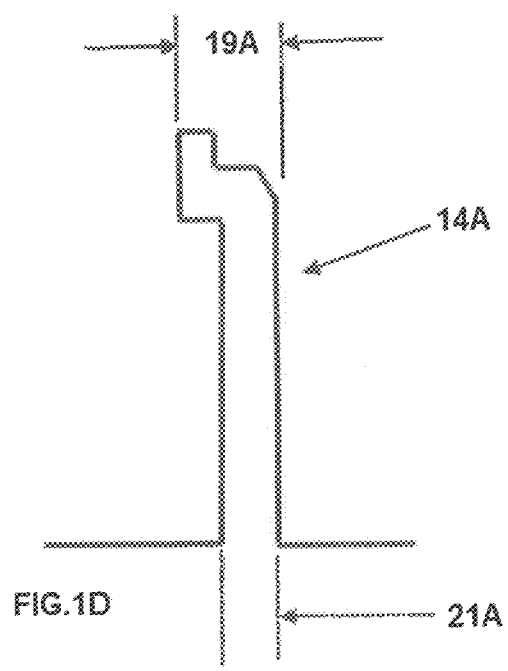

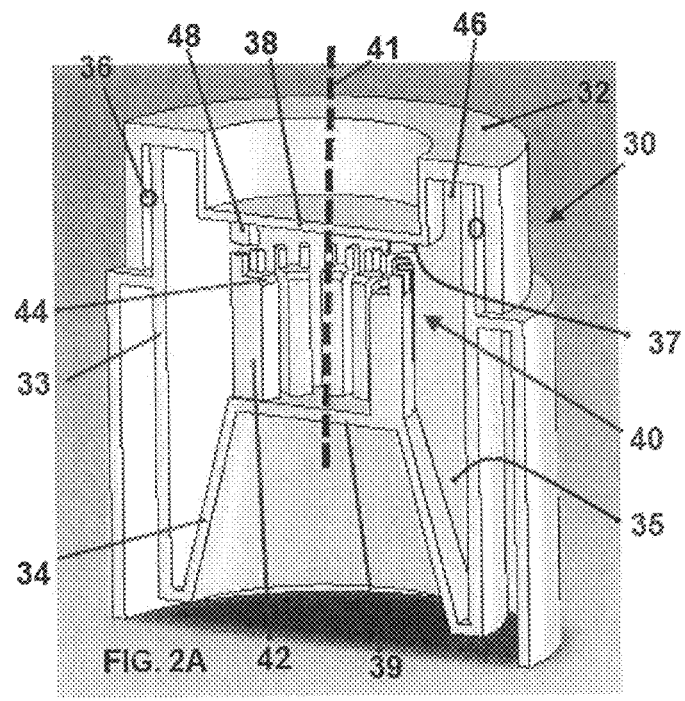
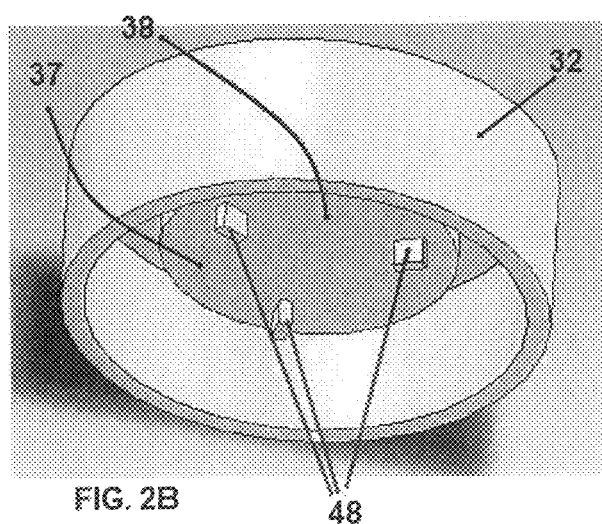

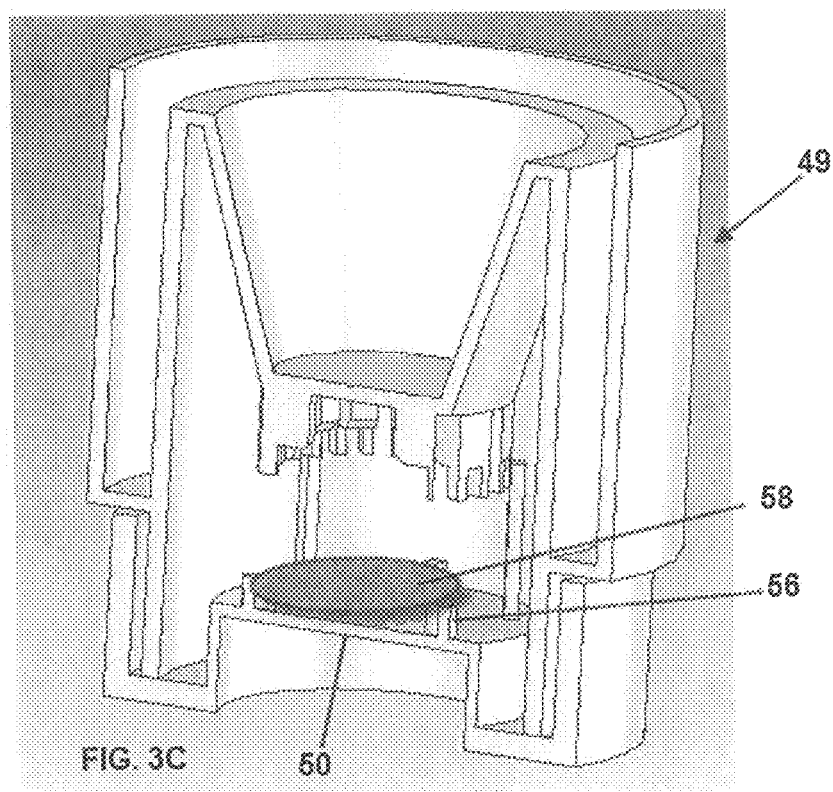

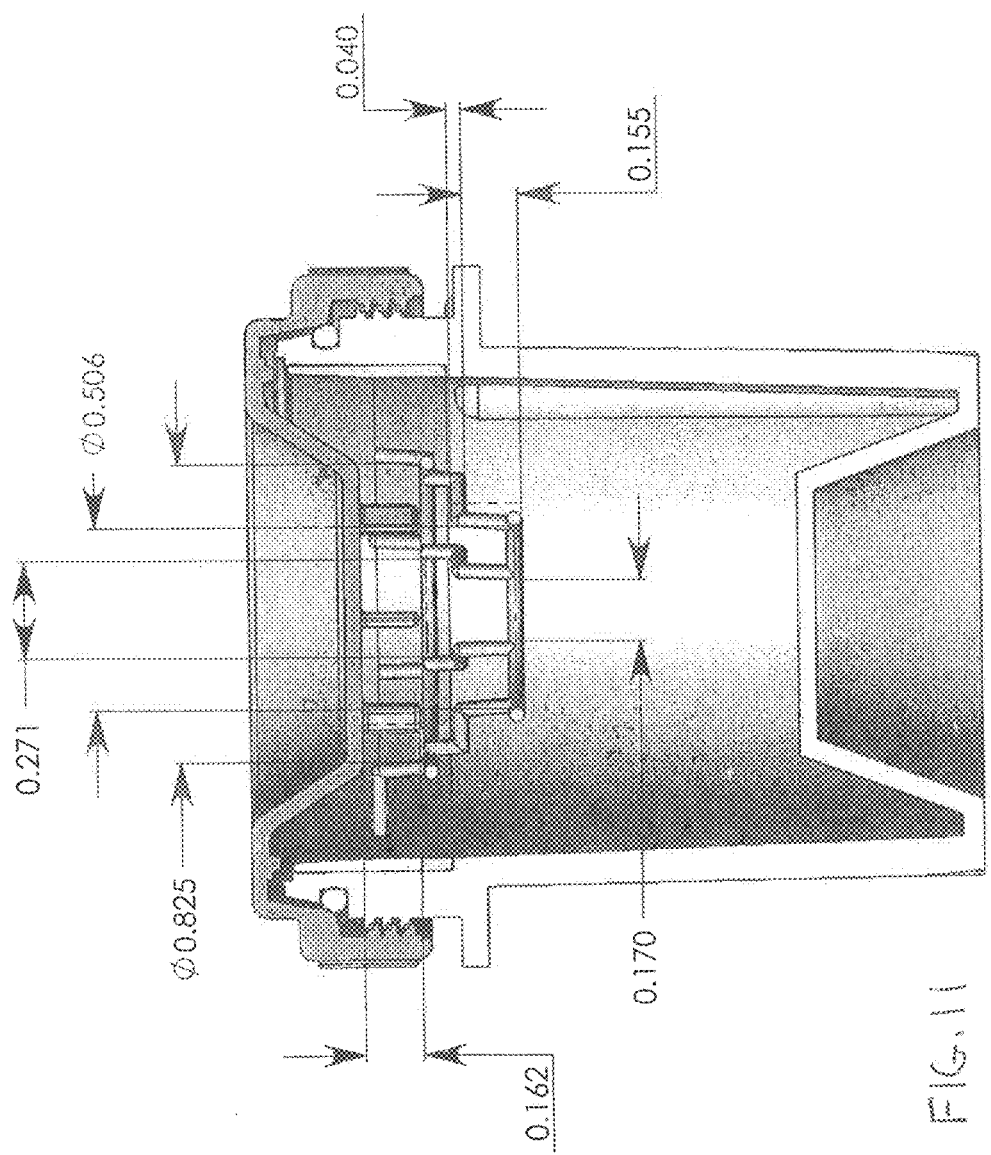

CORNEA STORAGE CONTAINER TO MAXIMIZE CORNEA HEALTH

RELATED APPLICATION

This application claims the benefit of priority of U.S. Provisional Application No. 61/187,919 filed Jun. 17, 2009, the disclosure of which is hereby incorporated by reference.

TECHNICAL FIELD

The technical field of this invention is related to devices and methods that improve cornea preservation.

BACKGROUND OF THE INVENTION

Each of the applications, patents, and papers cited in this application and in as well as each document or reference cited in each of the applications, patents, and papers (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein.

The cornea is the transparent structure that forms the anterior one sixth of the outer coat of the eye and is responsible for more than two thirds of its refractive power. The cornea consists of several layers, including the epithelium, stroma, and single-celled endothelium. The endothelium is the most posterior layer, interfacing with the aqueous humor of the anterior chamber of the eye. Corneal clarity is dependent on a relatively dehydrated state. The endothelium plays a key role in maintaining dehydration by both preventing aqueous humor from entering the cornea and by pumping fluid from the corneal stroma into the anterior chamber. Corneal endothelial cells do not replicate. When destroyed by disease or surgery, the remaining cells enlarge and spread out to cover the posterior corneal surface, thus decreasing the cell density (cell count). Corneas with extremely low endothelial cell densities can no longer maintain a dehydrated state. The corneas may decompensate, swell, and become cloudy over time, with an associated loss of visual acuity.

Cornea transplants are used to improve visual acuity by replacing the opaque or distorted host tissue by clear healthy donor tissue. The most common indication in this category is pseudophakic bullous keratopathy, followed by keratoconus, corneal degeneration, keratoglobus and dystrophy, as well as scarring due to keratitis and trauma. Donor corneas provide the source material for the transplants. Since the health of the cornea at the time of surgery has an impact upon outcomes, it is critical that the cornea container used to store the cornea from the time that it is harvested from the donor eye globe to the point at which it is used in surgery maintains the cornea in an optimal state of health. This need has become even more imperative as LASIK surgery, which renders donor corneas unsuitable for transplant, has become widely accepted in society. Thus, there is a shrinking source of donor corneas and less opportunity to be selective among donated corneas, putting even more importance on the capability of the cornea container to maintain optimal cornea health.

Once removed from the donor, corneas are placed in a cornea container, which is filled with preservation medium and delivered to an eye bank. The eye bank stores the cornea, performs quality assessments by way of slit lamp and specular microscopy, and delivers the cornea to a surgical location. The cornea container should allow the technician that harvests the cornea to easily deposit the cornea into the container, facilitate quality assessments, and make it easy for those performing surgery to easily remove the cornea from the storage container. Unfortunately, cornea containers that are used, or have been conceived, are suboptimal.

The earliest storage containers merely placed the cornea in a vial filled with preservation medium. However, there was no control over the position of the cornea, causing problems that included trapping the endothelium in a position that cut it off from the surrounding medium, allowing the epithelium to make contact with the walls of the vial, letting gas bubbles contact the cornea, and preventing lack of controlled positioning for specular microscopy and slit lamp evaluation. Although it was easy to deposit the cornea into the vial, the ability to easily retrieve the cornea was difficult.

The vial container was improved by attaching the cornea to the lid with a suture in order to allow easier removal of the cornea. But attaching the cornea to the suture required more handling of the cornea by those retrieving them from the donor. It still allowed the endothelium to become trapped in a position that cut it off from the surrounding medium, allowed the epithelium to make contact with the walls of the vial, let gas bubbles contact the cornea, and prevented lack of controlled positioning for specular microscopy and slit lamp evaluation.

In an attempt to overcome some of the problems of attaching a cornea to a suture, U.S. Pat. No. 4,695,536 describes a cornea container that retains the cornea in a fixed position within a medium vial. A steel wire is attached to the lid. An alligator clip is attached to the opposite end of the wire. The person retrieving the cornea attaches the sclera (the tough white opaque tissue that surrounds the cornea) to the alligator clip and carefully attaches the lid so the epithelium comes to reside upon a plurality of dividers that reside in the body of the cornea container. Although this configuration resolves some of the positioning problems of the suture approach, such as preventing the endothelium from being cut off from its media supply, the epithelium is forced to be in direct contact with the dividers that reside in the vial. Direct physical contact between the dividers and the epithelium can cutoff media access, affecting the health of the cells that comprise the epithelium, and can physically damage the epithelium as it is dragged across the dividers when the cornea is removed for surgical implantation. Also, the technician is required to transfer the cornea from forceps to the retaining clip in a manner that prevents damage to the cornea. That process can add contaminants to the container as the technician is likely to place their gloved hands directly upon the alligator clip to open it during the process rather than find a clever way to actuate the alligator clip with a sterile tool. Touching a component that resides within the container, even with gloves, is not good practice because bioburden level is dependent on what the technician's gloves have contacted previously and is also impacted by the skill level of the technician. Thus, the process of using this storage container increases contamination risk and is highly dependent on the skill and patience of the technician. Manipulation of the tissue by the technician may also damage the non-regenerating endothelium. Also, there is no geometry to prevent gas from contacting the cornea as the container is shipped, subjecting the cornea to potential damage in transit.

U.S. Pat. No. 4,844,242 also attempts to prevent the cornea endothelium from becoming trapped face down in a medium vial by orienting the cornea in a fixed position within the retaining lugs of a support ring. However, the harvesting process currently used to obtain donated corneas often leads to corneas of various diameters and rarely results in a completely circular excision. The apparatus '242 does not easily accommodate corneas of various diameters, or those that are not circular, since the support ring and the retaining lugs only allow about a 12% variation in cornea diameter before extra trimming is required. The more the cornea is handled for trimming, the more potential problems arise. For example, twisting, stretching, additional contact with forceps, and extra cutting increase the chances of damage to the tissue, particularly at its edges and on the endothelial cell surface. Furthermore, the outcome can vary from technician to technician since cutting the corneas to match the limited diameters accepted by the apparatus of '242 requires patience, time, and a high level of skill. In general, those obtaining donor corneas desire the least amount of preparation and exposure to the environment necessary before the cornea is placed into its medium storage container. Moreover, the act of using forceps to press the cornea into the retaining lugs of the support ring can inflict further damage to the cornea. Still another problem with the apparatus of '242 is that gas in the container has the potential to make contact with the cornea during shipping, and can even become trapped in direct contact with the endothelium depending on the orientation of the container.

For the reasons described, the US market has avoided the use of the free floating vial, and rejected sutured lids attached to a vial, as well as devices described in patents '536 and '242. Instead, the US standard is a cornea container that allows gravity to position the cornea in a basket that holds the cornea in a fixed location within the container. Throughout, we refer to the cornea container which has come to be the industry standard as a "conventional container". The conventional cornea container includes a corneal basket to hold the cornea. It has completely dominated the US market since at least the late 1980's. The conventional container achieves its popularity because it is so easy to place the cornea into the container's corneal basket and remove it from the container's corneal basket with forceps. Just placing the lid on the container automatically fixes the position of the cornea, the cornea is positioned for examination by slit lamp and specular microscopy, and the process is not highly dependent on the skill level of the technician.

In use, a technician merely drops the cornea, epithelial side down, into the medium filled container. The cornea gravitates to reside upon a corneal basket, formed of a group of prongs emanating from the base of the container that are arranged in a circular pattern. The corneoscleral disc resides upon the prongs in a position such that the plane in which the sclera resides in is generally parallel to the top and the bottom of the container. This allows examination of the cornea by slit lamp and/or specular microscopy. The lid is designed so that a portion of it functions as a viewing window. No matter the orientation of the container, the cornea is kept from falling out of the basket by the viewing window, which is typically only about 0.05 inches from the sclera. A relieved area in the lid acts as a gas trap and occupies the perimeter of the viewing window, controlling the location of gas within the container. A similar gas trap is present in the container. The cornea basket is positioned away from the container walls, allowing gas to move from the lid to the bottom of the container without contacting the corneoscleral disc as the conventional container is inverted.

The conventional cornea container was introduced by Coopervision Inc, Irvine Calif. The basket included eight prongs that rose from the bottom of the container. The corneoscleral disc resided in contact with the prongs. The container left room for improvement however. The basket design included prongs which obstructed the ability for slit lamp observation of the epithelium. Around the late 1980's, Bausch & Lomb entered the market with a conventional cornea container that allowed slit lamp observation. Their product is called the Independent Corneal Viewing Chamber™, and it came to dominate the US market.

Although the conventional cornea container has many advantages over any other proposed or previously tried cornea container, we have discovered that the design acts to limit cornea health. One problem, detailed within, is that the design of the corneal basket impedes the effective use of preservation medium within the container and as a result is suboptimal for maintaining corneal health. The other problem is that the lid design allows the sclera to become suctioned to it, thereby cutting off solute movement to the endothelium, and in some cases, even trapping gas against the endothelium.

A review of conventional container basket geometry helps clarify the problem of effective use of preservation medium within the container. When the cornea resides in the Coopervision cornea container, the prongs only provide a small open area between medium residing within the corneal basket and that outside of the corneal basket. The cross-sectional area of open space (about 0.69 in$^2$) for medium communication is exceeded by that of cross-sectional space occupied by prongs. There is only about 38% of the corneal basket open for preservation medium communication. The distance between prongs is also limited to about 0.1 inch, which acts to trap gas that may form during medium temperature increases as will be explained later. An additional problem exists with the width of the prongs, as measured from the inner diameter to the outer diameter of their basket arrangement. The width of the corneoscleral disc support section is virtually maintained constant from the base of the prong to the point of disc contact (i.e. along the height). That adds further resistance to medium communication. For example, the Coopervision prongs have a width of about 0.4 inches.

The same problems exist in Bausch & Lomb's Independent Corneal Viewing Chamber™, which will be detailed further within.

SUMMARY OF THE INVENTION

The present invention is a novel cornea container that can improve the health of corneas, as determined by quantitative specular microscope analysis of the human corneal epithelium with respect to endothelial cell shape and corneal thickness. Accordingly, it is an object of the present invention to provide improved conventional corneal containers that overcome the problems of conventional corneal containers in order to provide superior cornea health.

In one aspect of the present invention, projections emanate from the lid to prevent the cornea from becoming suctioned against the lid.

In another aspect of the present invention, a corneal basket comprised of a plurality of prongs and disc support surfaces allows the area between the disc support surfaces and the container base to have an open area greater than 38%, and more preferably at least 50%, to allow improved movement of solutes residing within the preservation medium.

In another aspect of the present invention, the corneal basket includes upper and lower disc support surfaces to allow a greater range of cornea sizes to reside in the container. The corneal basket is structured to allow the area between the upper disc support surfaces and the container base to have an open area greater than 38%, and more preferably at least 50%, to allow improved movement of solutes residing within the preservation medium.

BRIEF DESCRIPTION OF THE DRAWINGS

FIG. 1D shows an illustrative embodiment of the present invention in which a prong 14A includes a wider section and a narrower section.

FIG. 2A shows a cross-section of a perspective view of an illustrative embodiment of the present invention which can increase the cross-sectional area for solute movement to the endothelium while preventing the corneoscleral disc from contacting the lid.

FIG. 2B shows a perspective view of the lid including three lid projections which emanate from lid underside.

FIG. 3C shows cornea container inverted so that endothelium of corneoscleral disc resides in a second position and can be examined by specular microscopy. Second lid projections act to keep corneoscleral disc from becoming suctioned to lid.

FIG. 11 shows a cross-section of the embodiment used to gather the data and information presented in Example 1 and Example 2.

DETAILED DESCRIPTION OF THE INVENTION

The container that corneas reside in during transport and during storage at eye banks is often referred to as a corneal storage container, viewing chamber, and/or storage and viewing chamber. Thus, herein the words, or any combination of the words chamber, container, storage container, and viewing chamber mean the device that holds a cornea and preservation medium. Herein, bulk preservation medium also means the same thing as storage medium and preservation fluid. Herein the words, or any combination of words cornea, corneal, corneoscleral disc, disc, corneal tissue, or donor tissue mean the tissue that is harvested, stored, shipped and/or transplanted.

Figure 1A:
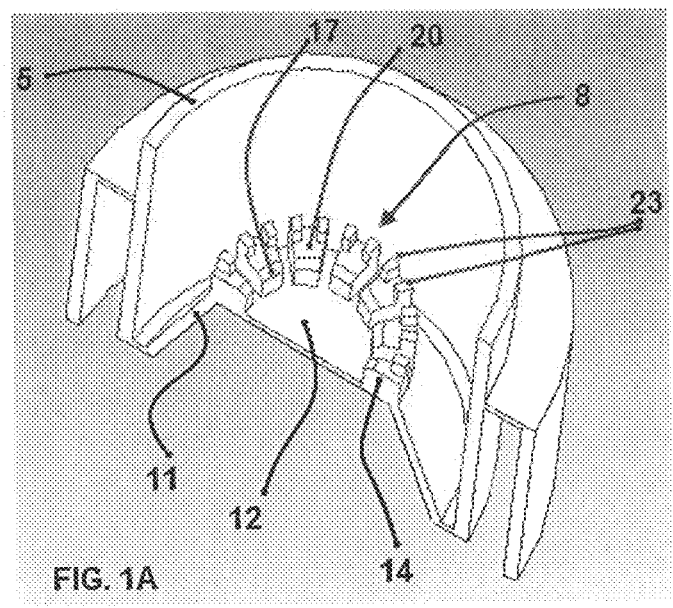
FIG. 1A shows a cross-sectional perspective view of the conventional Independent Corneal Viewing Chamber™.
Figure 1B:
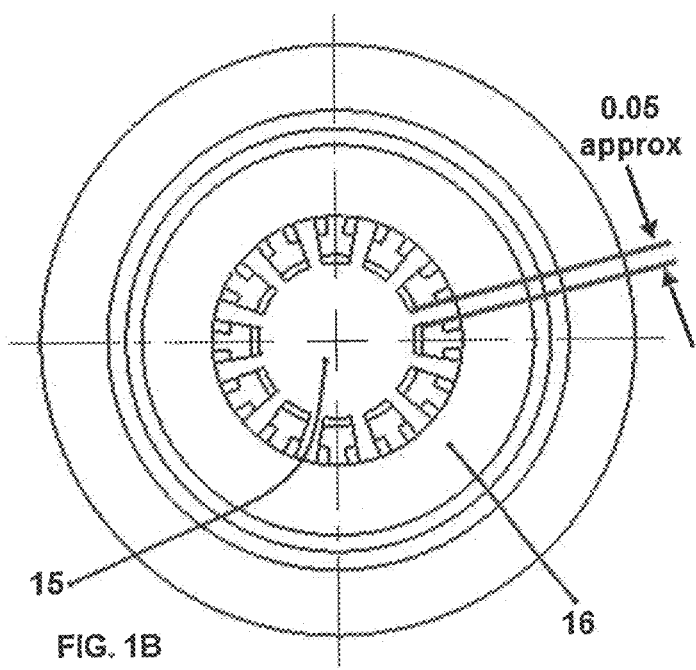
FIG. 1B shows a top view of the conventional Independent Corneal Viewing Chamber™.
Figure 1C:
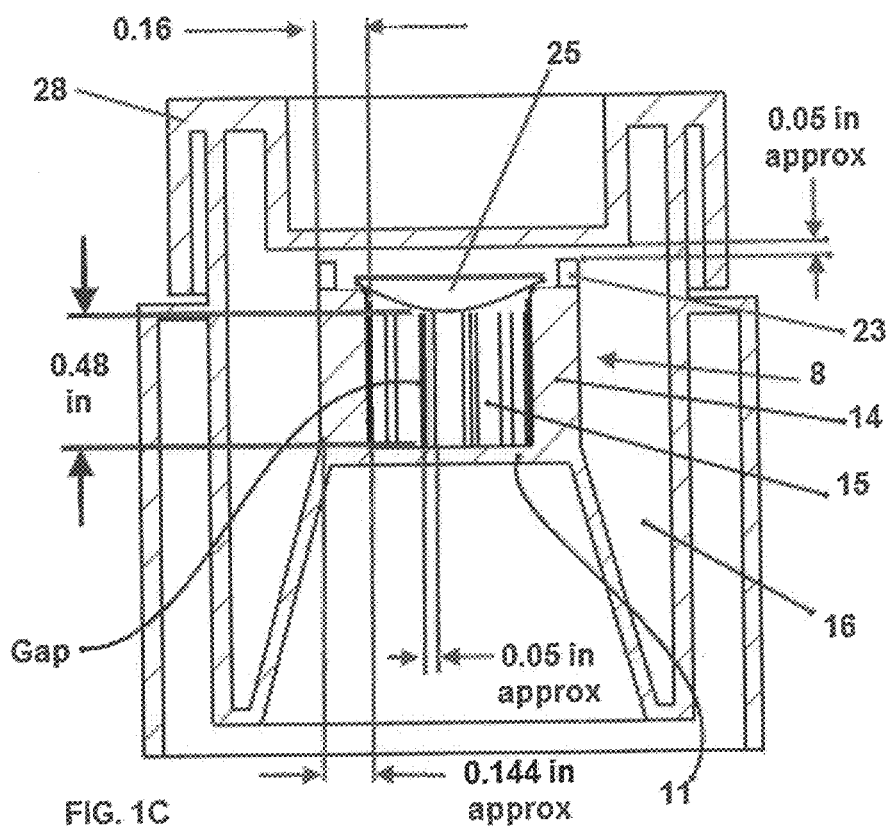
FIG. 1C shows a cross-sectional view of the conventional Independent Corneal Viewing Chamber™ with a cornea residing in it.

To help define the problems present in the conventional cornea containers, an assessment of Bausch & Lomb's Independent Corneal Viewing Chamber™ follows, aided by FIG. 1A, FIG. 1B, and FIG. 1C. FIG. 1A shows a perspective view of a cross-section of container 5 of the Independent Corneal Viewing Chamber™. The lid is not shown in order to clearly show the area in which the corneoscleral disc resides. Corneal basket 8 resides within container 5 and is attached to container base 11, which forms the bottom of container 5. Container base 11 includes a container viewing window 12 and corneal basket 8 occupies the perimeter of container viewing window 12. Corneal basket 8 includes twelve prongs 14 arranged in a radial (i.e. circular) manner upon which the cornea resides. Each prong 14 has a disc support surface 17 which is a beveled area that intends to generally conform to the cornea curvature, a flat section 20, and two cornea retention fingers 23 that rise from flat section 20 of each prong 14. Also, each prong 14 is attached to container base 11. In use, the cornea is oriented epithelium side towards container base 11 and typically makes physical contact with each disc support surface 17. The minimum distance between prongs 14, as best shown in the top view of FIG. 1B, is about 0.05 inches. Note that the distance between two adjacent prongs is measured as the shortest path between prongs. Throughout this specification, we refer to "open area" and "closed area." Open area is defined herein as the sum of the distance between adjacent disc support surfaces times the distance between the disc support surfaces to the container base. When the distance between support surfaces is referred to, it is the shortest linear distance between support surfaces. Thus, the open area is a measure of the ability for preservation medium to move to the volume of space beneath the cornea.

In use, prongs 14 act to surround a volume of preservation medium (inside preservation medium 15). Prongs 14 separate inside preservation medium 15 from outside preservation medium 16. Thus, as best shown in FIG. 1C, when a corneoscleral disc 25 resides upon prongs 14, preservation medium residing within corneal basket 8, (i.e. inside preservation medium 15) is blocked from communication with outside preservation medium 16 by corneoscleral disc 25 and by prongs 14. Thus, inside preservation medium 15 can only communicate with outside preservation medium 16 by way of the "open area" below each support surface upon which the disc resides. In the Independent Corneal Viewing Chamber™, the cumulative open area is about 0.342 in². Thus, about 0.342 in² of area is available for inside preservation medium 15 to interact with outside preservation medium 16, while about 0.616 in² is closed area blocked by prongs 14. Prongs 14 block more cross-sectional area between inside preservation medium 15 and outside preservation medium 16 than the open area provides. Thus, in use corneal basket 8 the amount of open area relative to the cumulative open area and closed area is only about 36%. Thus, only about 36% is open for liquid contact between inside preservation medium 15 and outside preservation medium 16.

Herein, we will demonstrate that improvements to corneal health can result from increasing the cross-sectional area for inside preservation medium 15 to interact with outside preservation medium 16. One approach is to merely alter the traditional Corneal Viewing Chamber™ design to increase the open area such as by eliminating prongs or increasing the distance between prongs. Other embodiments that improve upon the traditional design will be shown herein.

Also, interaction between inside medium and outside medium is further impeded by conventional container prong design, which includes a substantially uniform distance, past which preservation medium must travel for interaction between the inside preservation fluid and the outside preservation fluid. The standard uniform distance is best shown in FIG. 1C and is about 0.144. A superior prong design would retain the conventional geometry at the disc support surface and diminish said distance along the length of the prong between the disc support surface and the container base.

FIG. 1D shows a preferred embodiment of the present invention in which prong 14A includes a first width 19A which exceeds second width 21A. Preferably, second width 21A is generally uniform from the transition at first width 19A to container base 11A. Preferably, second width 21A is less than about 0.144 inches, more preferably less than 0.1 inch, and even more preferably less than about 0.06 inches. If structural strength is a concern, one or more prongs can allow second width 21A to exceed that of other prongs 14A, so long as at least the majority of prongs should integrate the narrower shape.

In conventional corneal basket design, the distance between prongs creates another problem. Preservation medium is often stored at 4° C. As medium temperature rises, which is often the case, its gas carrying capacity is reduced. Microbubbles form and rise. The microbubbles that form within the traditional corneal basket cannot easily escape because the limited distance between prongs causes surface tension barriers that will direct the bubbles to the epithelium side of the corneoscleral disc. This is another problem with the design of traditional cornea baskets. To ensure such problems don't exist, preferred minimum distance between disc support surfaces is 0.125 inches and more preferably 0.25 inches.

The epithelium is not the only area of the cornea that is impeded from access to the preservation medium. The endothelium is also, as best shown in FIG. 1C. Corneoscleral disc 25 is shown residing within corneal basket 8. A distance of about 0.05 inches exists between prongs 14 and lid 28. This distance is intended to allow a gap for movement of preservation medium to and from the endothelium. In actual use, when the sclera makes contact with the lid, as may be the case when the container is placed upside down, corneas have a potential to stick to the lid surface by suction. This can prevent preservation medium from accessing the endothelium of the cornea which can damage the tissue by limiting solute delivery, trapping waste products, and/or trapping gas against the endothelium. Furthermore, even if the cornea is not in contact with the lid, the total cross-sectional area by which medium can access the endothelium is quite limited as can be seen in FIG. 1C. This problem exists because conventional containers maintain the endothelium within the focal length of specular microscopes, even throughout transit and storage. The total cross-sectional area available for solute transport to the endothelium is typically the cross-sectional area between the cornea retention fingers of the prongs (this is best case since in use the cornea sclera can often block this area of mass transfer) plus the cross-sectional area from the top of the prongs to the lid, which cumulatively about 0.091 in².

In yet another problem with the device, the prongs are designed to make contact with the sclera, but no attempt is made to minimize contact. Thus, the physical area of the sclera that can be in contact with the prongs is typically the cumulative surface area of the disc support surface which is about 0.054 in². Physical contact can act to block mass transfer at the point of corneoscleral contact, further damaging tissue.

FIG. 2A shows a cross-section of a perspective view of an illustrative embodiment of the present invention which can increase the cross-sectional area for solute movement to the endothelium while preventing the sclera from contacting the lid. Corneal viewing chamber 30 includes lid 32 which is attached to container base 33 in a liquid tight manner. O-ring 36 resides between lid 32 and container base 33, providing a liquid tight seal of the contents when in use. Lid 32 includes lid viewing window 38, which acts to allow specular microscopy of the corneal endothelium. The bottom of container base 33 is formed by container bottom 34, which includes container viewing window 39, which acts to allow slit lamp examination of the corneal epithelium. Preferably, like conventional containers, container viewing window 39 resides in a second plane above the lowest plane of container bottom 34 to form container gas trap 35 and to prevent container viewing window 39 from being scratched. Container bottom 34 includes a corneal basket 40, which is a group of prongs 42 arranged in a radial pattern about the perimeter of container viewing window 39. Prongs 42 include disc support surface 44, which is an area upon which the corneoscleral disc is intended to reside. In this case, disc support surface 44 is the beveled area. The diameter of the circular prong arrangement is structured to hold corneas of various sizes. The range of cornea sizes is dependent on how they are excised from the eye globe, and whether or not the donor is an adult. Preferably, donated corneas can thus range in size from diameter of about 12 mm to about 23 mm. More preferably, the prongs are arranged to accept corneas with diameters from about 15 mm to 22 mm.

Lid 32 includes lid gas trap 46, which is a relieved area about the perimeter of lid viewing window 38. Lid gas trap 46 acts to trap gas in a location such that it does not encounter the cornea during transit. The depth of lid gas trap 46 is the difference between the lower plane in which lid viewing window 38 resides and the upper plane of the inside surface 37 of lid 32. Lid projections 48 emanate from lid underside 37, which is the surface of lid 32 that faces corneal basket 40. Lid projections 48 act to prevent the corneoscleral disc from attaching, or suctioning, to lid underside 37 during transit, handling, or specular microscopy viewing. To accomplish this objective, any number of lid projections 48 can emanate from lid 32. For example, just one lid projection 48 can prevent the periphery of the cornea from becoming suctioned to the lid. The use of three lid projections 48 allows the cornea to be retained a uniform distance from the lid, thereby allowing a uniform cross-sectional area for solute transport even if the cornea container is positioned upside down during shipping. This can also retain the sclera in a plane generally parallel to lid viewing window 38 and container viewing window 39. Since corneas are often removed from the donor in a manner that renders them non-circular, more lid projections 48 can help ensure that the periphery of the cornea makes contact with at least three projections. In the preferred embodiment, as seen more clearly in FIG. 2B which shows a perspective view of lid 32 removed from the container base, three lid projections 48 emanate from lid underside 37 of lid 32. Although the lid projections can be any shape, in the preferred embodiment the lid projections 48 are rectangular in shape and oriented with the long edge directed towards a common center point. The common center point preferably is center axis 41 of corneal basket 40 (see FIG. 2A). Thus, lid projections 48 are preferably arranged in a radial pattern about lid viewing window 38 to allow maximum assessment of the endothelium by specular microscopy. The lid projections 48 should be of sufficient diameter or width and/or length to interface with the dimensions of the corneal basket. Thus, if the corneal basket is designed to hold corneas of 15 mm at a minimum, as preferred in the above description, the narrowest diameter of the lid projections, as measured by the diameter closest to the axis would be slightly less than 15 mm, for example 13 mm, in order to ensure the sclera of a corneoscleral disc with a 15 mm diameter contacts a lid projection. The greatest diameter of the lid projections should slightly exceed the expected diameter of the donated tissue. For example, in the case of an expected 23 mm cornea tissue, the outer diameter of lid projections 48 would be at least about 24 mm. Then, in this example, the length of each lid projection 48 would be about 5.5 mm [i.e. (24 mm-13 mm)/2]. The width of each lid projection 48 should be narrow, so that medium access to the endothelium is not inhibited. Preferably, the width is less than about 1 mm.

If lid projections are just to break suction, a preferred distance is greater than about 0.02 inches. However, as the lid projections extend further from the lid there is an increase in cross-sectional area available for solute movement to the endothelium of the cornea as the distance between the sclera and the lid increases. If the lid projections are structured to maximize cross-sectional area for solute movement, they preferably do not extend a distance from the lid that prohibits specular microscopy. Thus, in a preferred embodiment for improved endothelium health, the lid projections place the entire endothelium in view of the specular microscope while maximizing the cross-sectional area for solute movement to the endothelium. Thus, the distance that the lid viewing window resides from the specular microscope lens, the thickness of the lid viewing window, the distance that lid projections emanate from the lid and the curvature of the cornea should be considered. For example, assuming that the specular microscope could focus at a maximum distance of 0.47 inches beyond the outside surface of the lid at the region of the lid viewing window, and assuming the furthest distance that the endothelium resides from the plane of the sclera is about 0.15 inches, and assuming the material thickness of the lid viewing window is about 0.06 inches, then lid projections should emanate a maximum distance of about 0.26 inches in order to maximize solute access to the endothelium while retaining the ability to assess the entire endothelium by specular microscopy. The length of the prongs of the corneal basket should be adjusted according to the distance that the lid projections emanate from the lid. At the point where the lid is secured in a liquid tight manner to the container base, a gap between the lid projections and the corneal basket exists and is preferably about 0.05 to 0.1 inches.

Figure 3A:
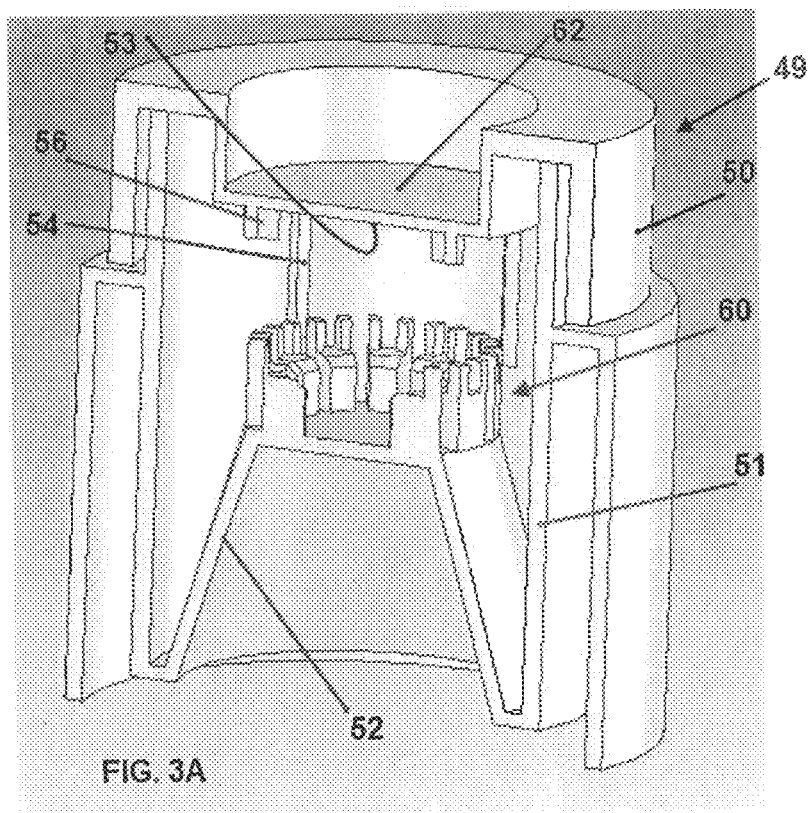
FIG. 3A shows a cross-section of the perspective view of another illustrative embodiment of the present invention. Cornea storage container is shown with lid attached to container base. First lid projections and second lid projections emanate from lid.
Figure 3B:
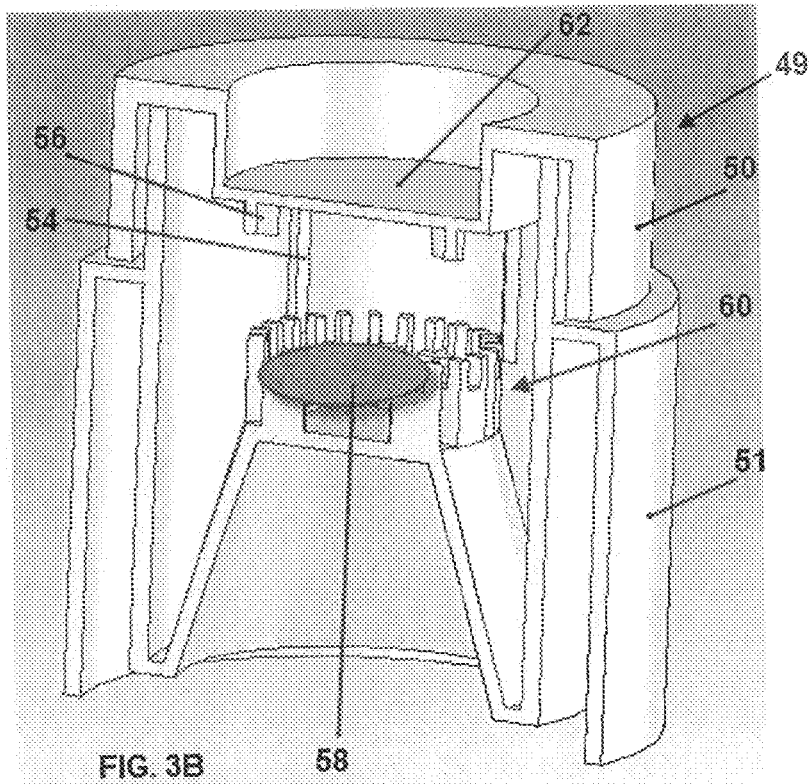
FIG. 3B shows corneoscleral disc residing upon corneal basket at a first position well beyond the focal length of a specular microscope.

One of the limits of conventional cornea containers is that the cornea is always positioned within the focal distance of a specular microscope, even when the cornea is not being examined by specular microscopy. That has the effect of limiting bulk preservation medium from access to the cornea endothelium during transit and storage. FIG. 3A, FIG. 3B, and FIG. 3C show views of an illustrative embodiment that, unlike conventional containers, allows the cornea to reside at a distance far beyond the focal length of a specular microscope during transit and storage, while retaining the ability to assess the cornea by specular microscopy. In this manner, bulk medium has greater access to the endothelium of the cornea during transit and storage. In essence, the cornea container is configured to allow the cornea to reside in either of two positions by the use of gravity. The cornea can reside in either a first position, in which the cornea resides upon a corneal basket that is at a distance far beyond that of the specular microscope focal length, or a second position in which the cornea resides within the focal length of the specular microscope.

In the cross-section of the perspective view of FIG. 3A, cornea container 49 is shown with lid 50 attached to container base 51, the bottom of container base 51 is formed by container bottom 52. First lid projections 54 and second lid projections 56 emanate from lid underside 53 of lid 50. In FIG. 3B, corneoscleral disc 58 is shown residing upon corneal basket 60 at a distance well beyond the focal length of a specular microscope. Thus, relative to the illustrative embodiment of FIG. 2A and FIG. 2B, an even more expansive open area is available for delivery of solutes and removal of waste from the endothelium. The increase in open area can be attained by increasing the distance from the top of the prongs to the lid beyond 0.05 inches and more preferably beyond 0.20 inches. Another element of the configuration is that features are present that ensure the cornea remains capable of being positioned epithelial side down upon the corneal basket. First lid projections 54 have the purpose of retaining corneoscleral disc 58 in a position so that it can return to its resting position upon corneal basket 60 after cornea viewing chamber 49 is inverted during shipping or specular microscopy. First lid projections 54 reside equal to or a small distance outside the diameter of corneal basket 60 such that when cornea container 49 is inverted for specular microscopy, first lid projections 54 do not obstruct the path of corneoscleral disc 58 as it moves towards lid viewing window 62 and comes to reside upon second lid projection(s) 56. Design considerations for second lid projections 56 are as previously described. A preferred embodiment utilizes at least three first lid projections, oriented in a circular pattern about the corneal basket, to ensure the cornea is capable of moving to the center portion of the lid viewing window and returning to the corneal basket. More first lid projections can be used, but be aware that the open area should exceed 36%, and more preferably exceed 50%. As shown in FIG. 3C, cornea viewing chamber 49 has been inverted so that cornea 58 can be examined by specular microscopy. Second lid projections 56 act to keep cornea 58 from becoming suctioned to lid 50. The number of second lid projections 56, and the distance that second lid projections 56 emanate from lid 50 are intended to keep the sclera of cornea 58 from making complete peripheral contact with lid 50. Although only one second lid projection is needed to prevent suction from occurring, three second lid projections are preferred to make it very likely the sclera makes contact with at least one projection in order to prevent suctioning. Skilled artisans will recognize that sclera may not be circular, as the shape is determined by the skill and patience of the person removing the donated cornea from the eye globe. The distance that the second lid projections emanate from the lid need only be about 0.020 inch to prevent suction. However, as is typically the case, the cornea container can become inverted during transport. Thus, extending the distance between the second lid projections and the lid viewing window to the maximum distance that allows specular microscopy, as described previously, ensures maximum solute movement to the endothelium during transport. To minimize the potential for the cornea to invert its position when the cornea container is inverted during transport or specular microscopy, the distance from the corneal basket location upon which the cornea resides to the second lid projections should be less than the diameter of a typical cornea. In this manner, the cornea has little chance of rotating to a position in which the epithelium side is oriented towards the lid. Thus, with the range of donor corneas at a diameter generally between about 12 mm and 23 mm, and typical diameters in the range of about 15 to 22 mm, a distance of between 15 mm and 22 mm is preferred, and more preferably about 15 mm to eliminate the potential for most donor corneas to become inverted.

Figure 4:
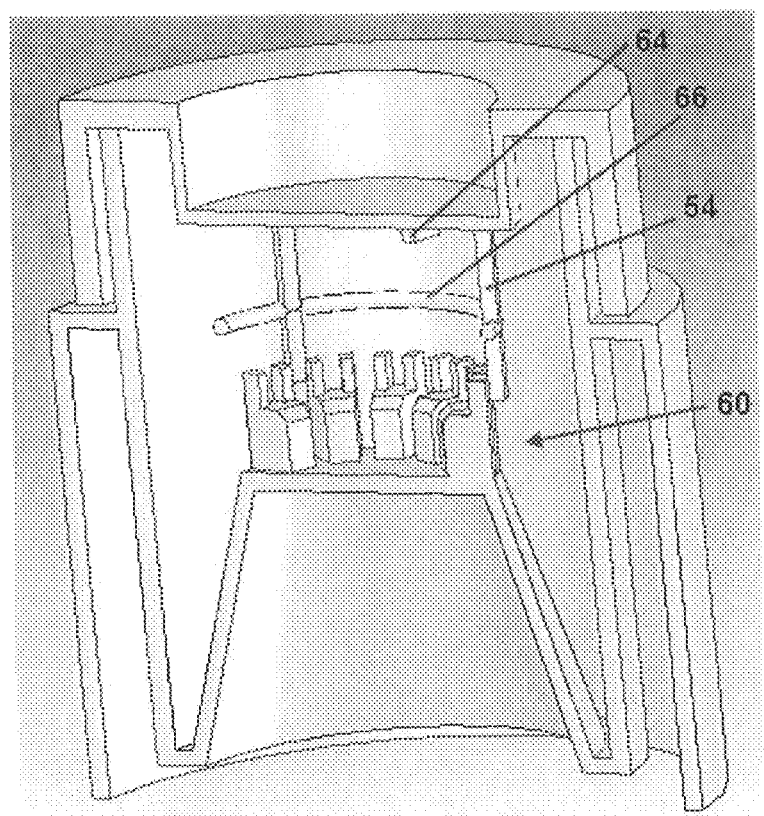
FIG. 4 shows a perspective view of how a band(s) of material can circle first lid projections to prevent the cornea from slipping past first lid projections when it departs from corneal basket. In this illustrative depiction, retaining band bridges the gap between first lid projections.

When there is a concern that the corneoscleral disc can rotate into a position that allows it to slip through first lid projections, more first lid projections can be added. Alternatively, a band(s) of material can circle the first lid projections to prevent the cornea from slipping past the first lid projections as shown in the cross-section of the perspective view of FIG. 4. Retaining band 66 bridges the gap between first lid projections 54. Although more than one retaining band 66 can be present, in the preferred embodiments the volume of space that the band(s) displace is minimized to maximize the area for solute movement in the media. Again, as described previously, open area should exceed 36%, and more preferably 50%. Thus, as shown, one retaining band 66 is present and is located at a distance about halfway between corneal basket 60 and second lid projections 64. Retaining band 66 need not completely circle first lid projections 54 so long as the open space is less than the diameter of a corneoscleral disc in order to prevent the disc from falling to a location at which it cannot return to the corneal basket.

Figure 5:
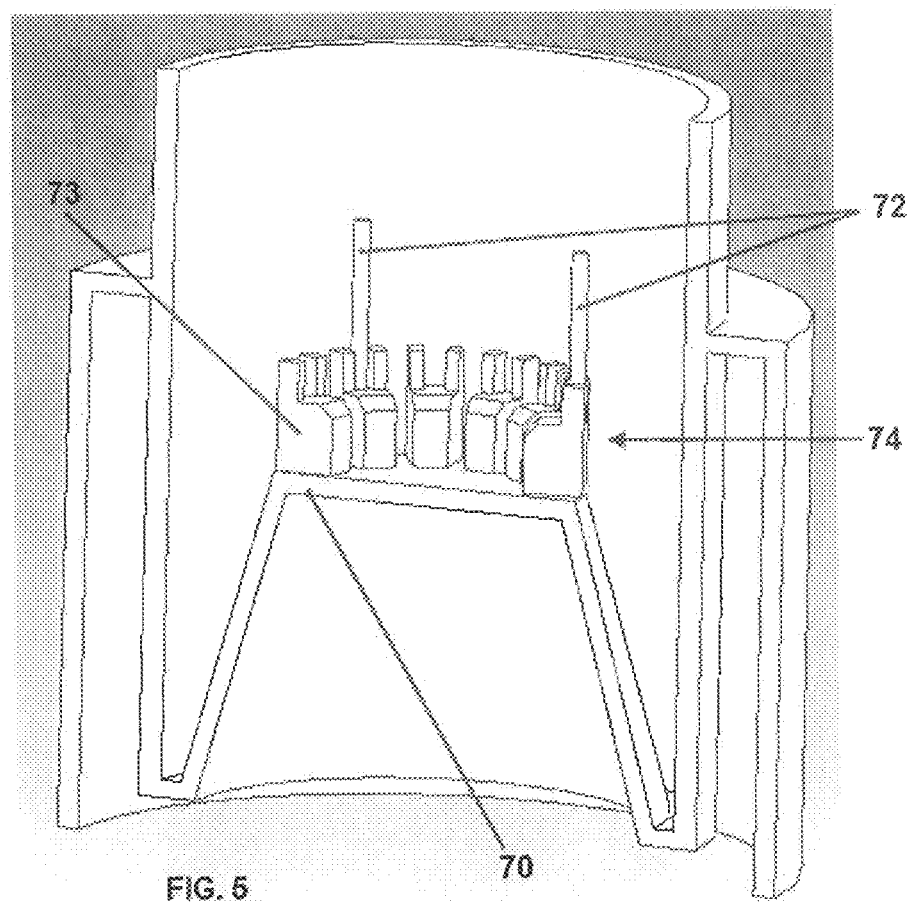
FIG. 5 shows a cross-section of a perspective view of an illustrative embodiment demonstrating how cornea retaining posts, as structure attached to or integral to corneal basket, can achieve the purpose of guiding corneas to the lid when the viewing container is inverted to place the cornea in a second position, and back to prongs when the viewing chamber is in the normal upright position where the cornea resides in a first position.

Guiding corneas to the lid when the viewing container is inverted need not only be accomplished by first projections emanating from the lid. Structure attached to, or integral to, the corneal basket can achieve that purpose. FIG. 5 shows a cross-sectional view of an illustrative embodiment of this approach. The lid is not shown for clarity. Corneal basket 74 emanates from container base 70 and includes cornea retaining posts 72 which emanate from corneal basket 74. Alternatively they may emanate from container base 70. Preferably, at least three cornea retaining posts 72 are present and they are equally spaced about corneal basket 74, reaching nearly to the lid or the lid projections, so that the cornea does not escape the confines of cornea retaining posts 72.

The barriers that conventional corneal baskets present to medium communication have been described in FIG. 1A, FIG. 1B, FIG. 1C and associated text. Referring again to FIG. 1B for example, inside preservation medium 15 is in limited communication with outside preservation medium 16. We have discovered that this conventional corneal basket design is diminishing the health of the cornea. Thus, an objective of this invention is to reduce or eliminate the barriers to communication of preservation medium residing in the area below the corneoscleral disc (i.e. inside preservation medium) and preservation medium outside the area below the corneoscleral disc (i.e. outside preservation medium). We have already disclosed preferred modifications that retain the traditional use of prongs that are continuous from the container base to the disc support surface. Embodiments that deviate from the traditional use of prongs are now disclosed.

Figure 6:
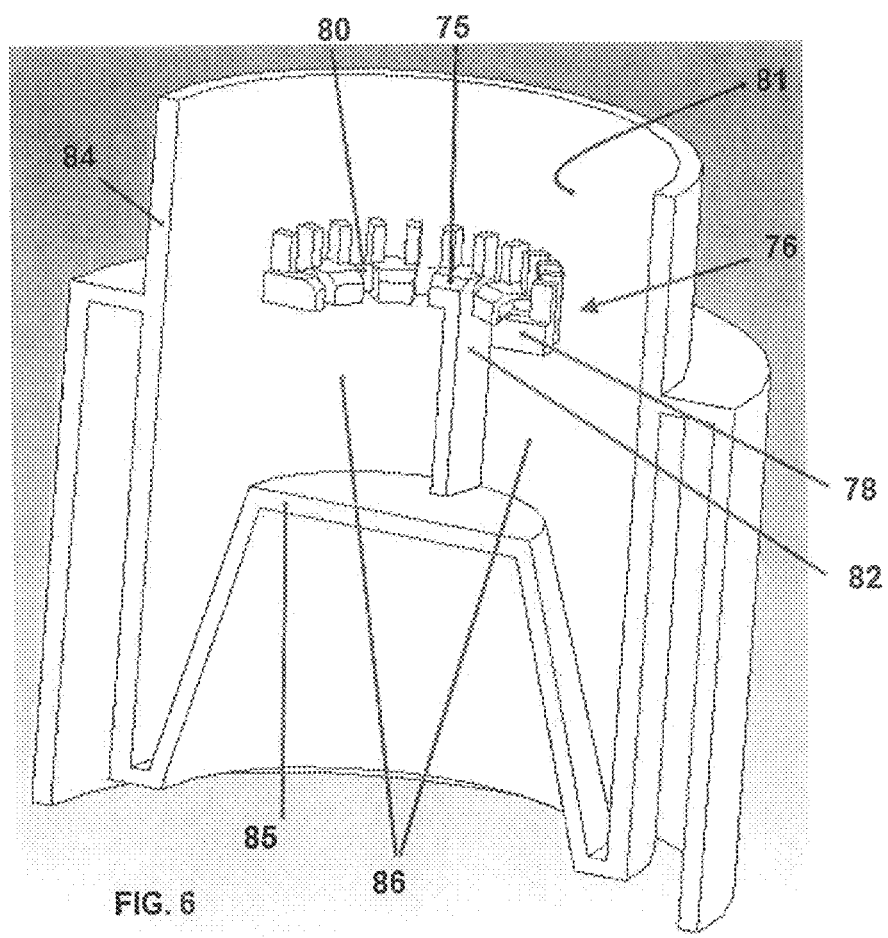
FIG. 6 is a cross-section of a perspective view of an illustrative embodiment of the present invention in which the traditional corneal basket has been altered in such a manner that allows more exposure of the cornea to preservation medium. Modified cornea basket includes medium access windows.

One type of modification to the conventional basket is to provide more open area by making at least one window through the corneal basket. Thus, this approach breaks with the traditional approach in which all prongs emanate from the container base and are a continuous structure between the disc support surface and the container base. FIG. 6 is a cross-sectional view of an illustrative embodiment of the present invention in which the traditional corneal basket has been altered in such a manner to allow open area. For clarity, the lid has been removed. As shown, unlike the conventional cornea storage container, not all prongs make contact with the container base. Modified corneal basket 76 includes modified prongs 78 configured with disc contact surfaces 75 that act to hold a cornea in a planar position. Preferably at least one, more preferably all but one, and ideally all of modified prongs 78 terminate without direct contact with container base 84. Modified prongs 78 are joined together by prong connection ring 80. Support posts 82, which can optionally be an extension of one or more prongs 78, mate modified corneal basket 76 to container base 84. One or more support posts 82 can be relied upon. Although modified corneal basket 76 is shown mated to container base 84, it can attach to any surface within container base bottom 85 such as inner container wall 81. In the event that modified corneal basket 76 is attached to inner container wall 81, the outer diameter of corneal basket 76 is preferably not directly in contact with inner container wall 81 so that gas can move between modified corneal basket 76 and inner container wall 81 when the position of the corneal storage chamber is inverted. A distance of at least 0.1 inch is preferred. Modified corneal basket 76 increases the open area for communication of preservation medium directly below the corneoscleral disc (previously referred to as "inner preservation medium") with the preservation medium not directly under the corneoscleral disc (previously referred to as "outer preservation medium"). Preferably the open area is greater than 38%, and more preferably at least 50%, of the open plus closed area. In essence, a medium access window is formed below the corneal basket. In this depiction, medium access window 86 is bounded on the sides by post 82, on the top by modified prongs 78 and prong connection ring 80, and on the bottom by container bottom 84. In this embodiment, easy deposit and retrieval of the cornea afforded by the conventional container is retained, while at least the epithelium of the cornea is provided with much improved access to preservation medium. Also, prong connection ring 80 allows the number of prongs 78 of modified corneal basket 76 to be reduced relative to conventional cornea baskets, since it can be located in any manner necessary to prevent the corneoscleral disc from falling between prongs 78 or below modified corneal basket 76. In the preferred embodiment, at least three prongs 78, and more preferably six prongs 78 are present. Preferably, disc support surfaces 75 of prongs 78 are capable of holding corneas in the range of about 15 mm to 22 mm. The container lid is preferably structured with lid protrusions as described previously. Distances that the cornea can reside from the lid can range to that within the focal length of a specular microscope throughout transit or can be increased by the use of first projections about the modified corneal basket as previously described.

Figure 7A:
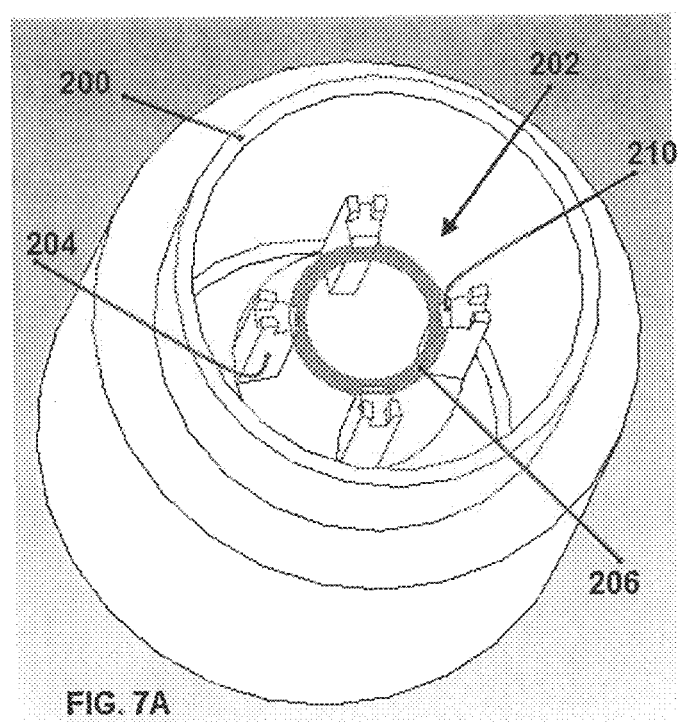
FIG. 7A is a top perspective view indicating how use of a prong connecting ring can prevent the corneoscleral disc from falling from the corneal basket in order to create far superior communication between inner preservation medium and outer preservation medium.

Another way to improve the conventional corneal basket is to widen the space between prongs, or eliminate prongs, while ensuring that the corneoscleral disc does not fall to the bottom of the container. The conventional corneal basket relies on prongs that are closely spaced together to prevent this event. FIG. 7A shows an illustrative embodiment indicating how use of a prong connecting ring can prevent the corneoscleral disc from falling from the corneal basket in order to create far superior communication between inner preservation medium and outer preservation medium. Modified cornea basket 202 resides within container base 200. Prong connecting ring 206 is adjoined to prongs 204. Prong connecting ring 206 acts to reduce the number of prongs needed relative to the conventional cornea basket because prong connecting ring 206 will make contact with the sclera if there is an attempt to place the corneoscleral disc onto the prongs in a manner that would allow it to otherwise fall to the bottom of container base 200. Preferably three prongs are present. Whatever number is used, care should be taken to ensure that at least 38%, and more preferably at least 50%, open area exists.

Figure 7B:
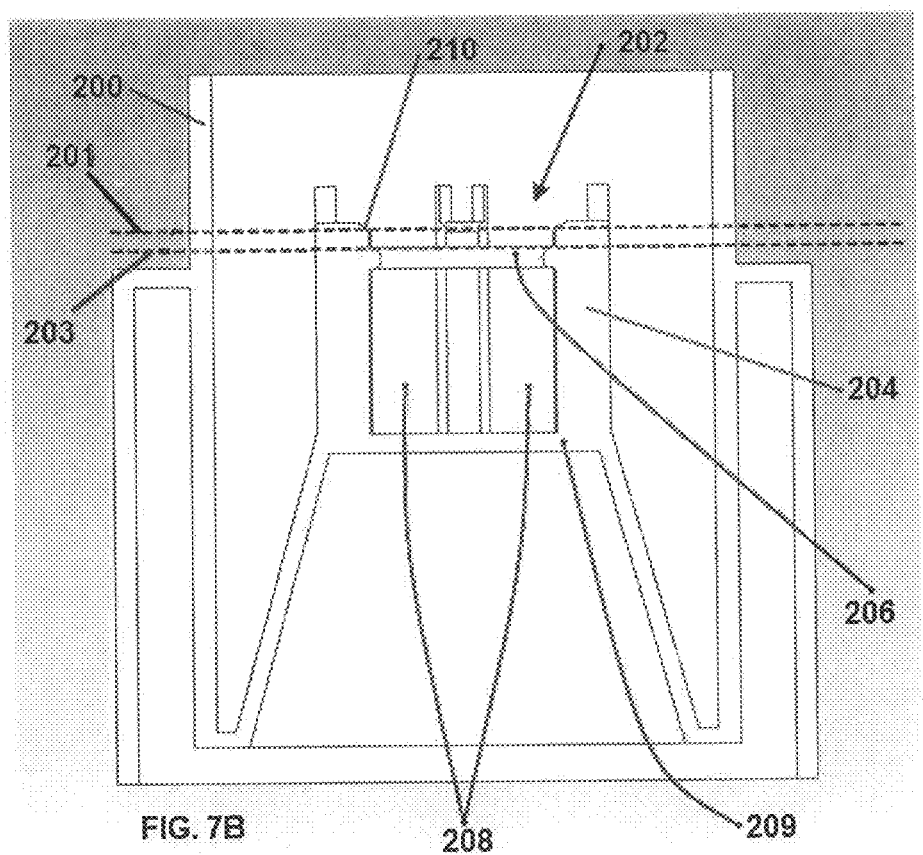
FIG. 7B is a cross sectional view showing how cornea basket windows allow a large gap for the inner preservation medium to interact with the outer preservation medium.

As shown in the cross-sectional view of FIG. 7B, cornea basket windows 208 can allow a large open area for the inner preservation medium to interact with the outer preservation medium. Preferably, prong connecting ring 206 resides in a plane below that of disc support surface 210 so that the corneoscleral disc does not make contact with prong connecting ring 206. In this case, prong connecting ring 206 resides in plane 203 which is below plane 201 in which disc support surface 210 resides. Thus, preferably prong connecting ring 206 does not make physical contact with the corneoscleral disc during use. When creating connecting ring 206, care should be taken to ensure that at least 38%, and more preferably at least 50%, open area exists.

Figure 8A:
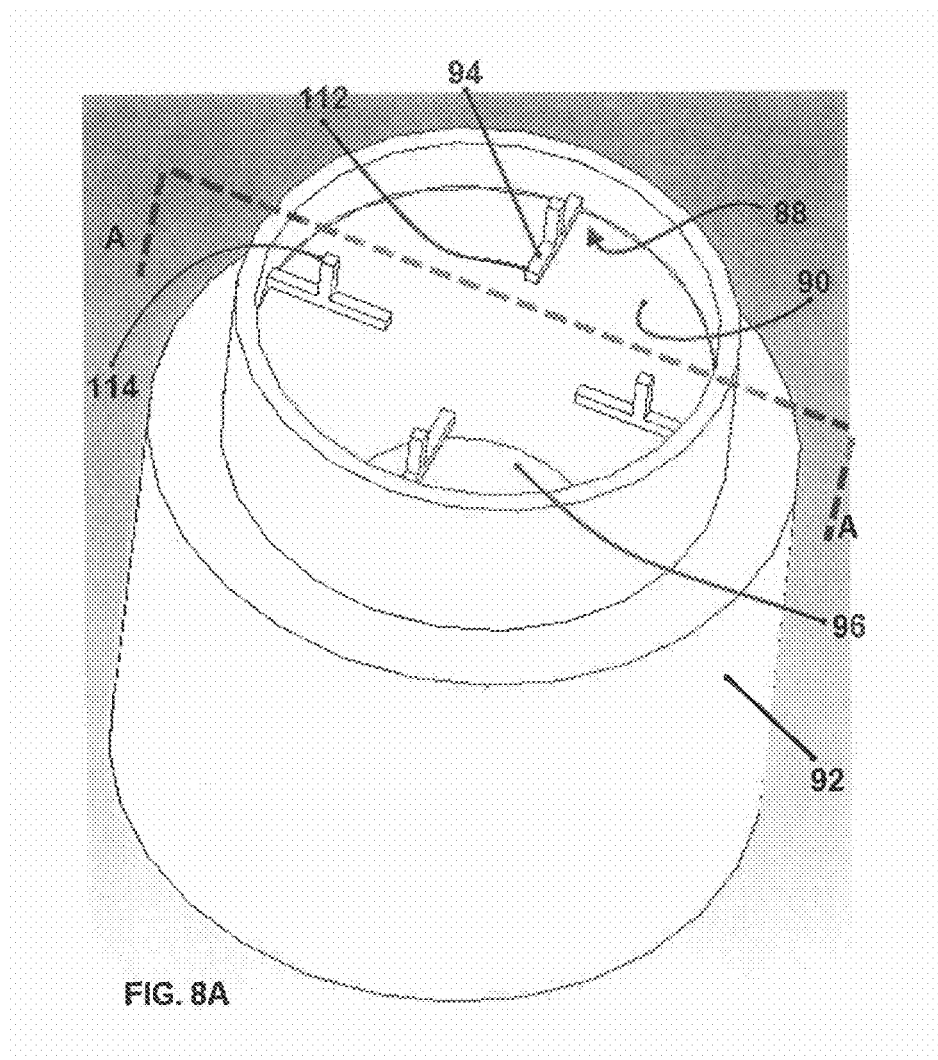
FIG. 8A shows an illustrative embodiment of the present invention disclosing corneal basket that minimizes contact with the cornea and greatly improves cornea access to bulk preservation medium.
Figure 8B:
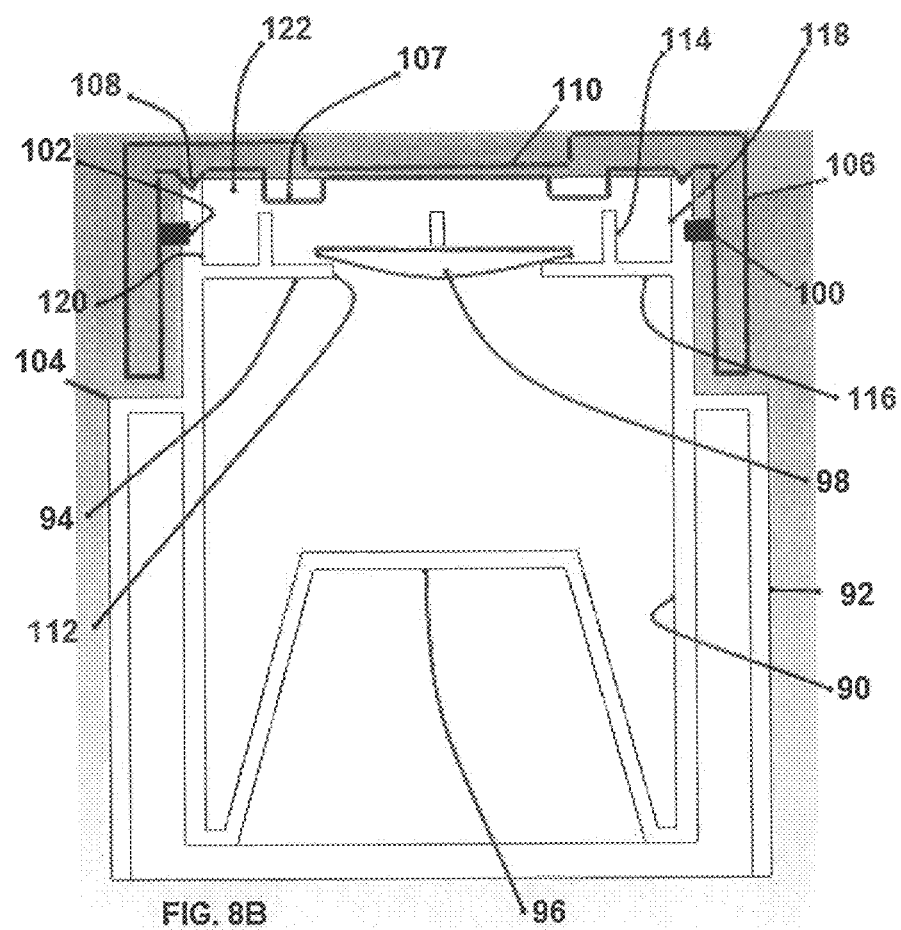
FIG. 8B shows cross-sectional view A-A of the illustrative embodiment of FIG. 8A with corneoscleral disc residing within it. Cornea retention posts can interact with lid to retain cornea in a desired position.

In yet another embodiment of the present invention, a unique configuration for a corneal basket that minimizes contact with the cornea and can greatly exceed the 38% open area of the conventional cornea container by allowing open area to be up to 100% is disclosed. FIG. 8A shows a perspective view of an illustrative embodiment of the present invention in which the lid has been removed for clarity. FIG. 8B shows cross-section A-A of FIG. 8A when the lid is attached. Corneal basket 88 is attached to inner sidewall 90 of container base 92. Skilled artisans will recognize that there are numerous options for attaching corneal basket 88 to inner sidewall 90 in order to retain it in a fixed position. In the preferred embodiment, corneal basket 88 is designed to hold the cornea such that the endothelium is oriented towards the lid. The distance between the furthest section of the endothelium is such that it does not exceed the focal length of a standard specular microscope as previously described. Corneal basket 88 is structured to allow the endothelium relatively unrestricted access to preservation medium and unimpeded slit lamp view of the epithelium, via container viewing window 96. The sclera of the cornea resides upon disc support surfaces 112, which are in essence the ends of cornea support rods 94. Four disc support surfaces are shown to aid the description of the cross-sectional view, but preferably, at least three disc support surfaces are present, each at the same distance from the specular microscopy window so that the cornea periphery resides in a plane parallel to the lid viewing window. Each disc support surface is preferably oriented in a circular pattern at uniform intervals about the cornea. Preferably, as with all of the embodiments of this invention, the cumulative surface area of the disc support surface that make physical contact with the cornea is less than that of a conventional corneal basket, or at least less than about 0.054 in$^2$. For example, when three cornea support rods 94 with a diameter of 0.04 inches are present, the amount of contact with the cornea is far less than that of traditional corneal baskets. Cornea retention posts 114 are preferably oriented in a vertical direction relative to the plane at which the cornea resides and act to keep the cornea from moving sideways, thereby keeping the cornea centered in corneal basket 88. The distance between disc support surfaces 112 is structured to prevent the cornea from falling through corneal basket 88 and to minimize the potential for contact with the cornea itself as opposed to the sclera. In a preferred embodiment, the distance between cornea retention posts is structured to accommodate corneoscleral discs in the size range of about 15 mm to about 22 mm.

The primary seal is provided by o-ring 100, which resides in o-ring gland 102 of container base 92. O-ring 100 is compressed by container base 92. A secondary seal is created as lid seal projection 108 makes physical contact with lid 106. Lid viewing window 110 allows specular microscopy. Cornea retention posts 114 can interact with lid 106 to trap cornea 98 in a desired position. In a preferred position the endothelium of cornea 98 is within focal length of a specular microscope. In this case, lid projections 107 are integrated into lid 106 to prevent the cornea from becoming stuck to lid 106. Preferably, cornea retention posts 114 should terminate with less than about a 0.1 inch gap, and even more preferably less than about a 0.05 inch gap, from the adjacent portion of lid 106 (in this case lid projections 107) to keep the cornea from moving out of corneal basket 88. Centering rods 116 act to mate cornea retention posts 114 to basket retaining ring 118 and act to locate disc support surfaces 112 in a desired position relative to lid 106. Centering rods 116 serve to ensure that the sclera does not move into the region below lid gas trap 122 in order to prevent, or greatly minimize, the possibility of gas contact with the endothelium. Thus, centering rods 116 preferably place all cornea retention posts 114 in a position such that they are never directly below lid gas trap 122. Although only one centering rod 116 can be present, at least three are preferred in order to provide stability throughout transit. Also, centering rods 116 can be in any position relative to disc support surface 112, centering rods 116 are preferred position equal to or below the height of disc support surface 112 so that centering rods 116 do not wick gas to the area above cornea 98 when the cornea container is inverted.

Figure 9:
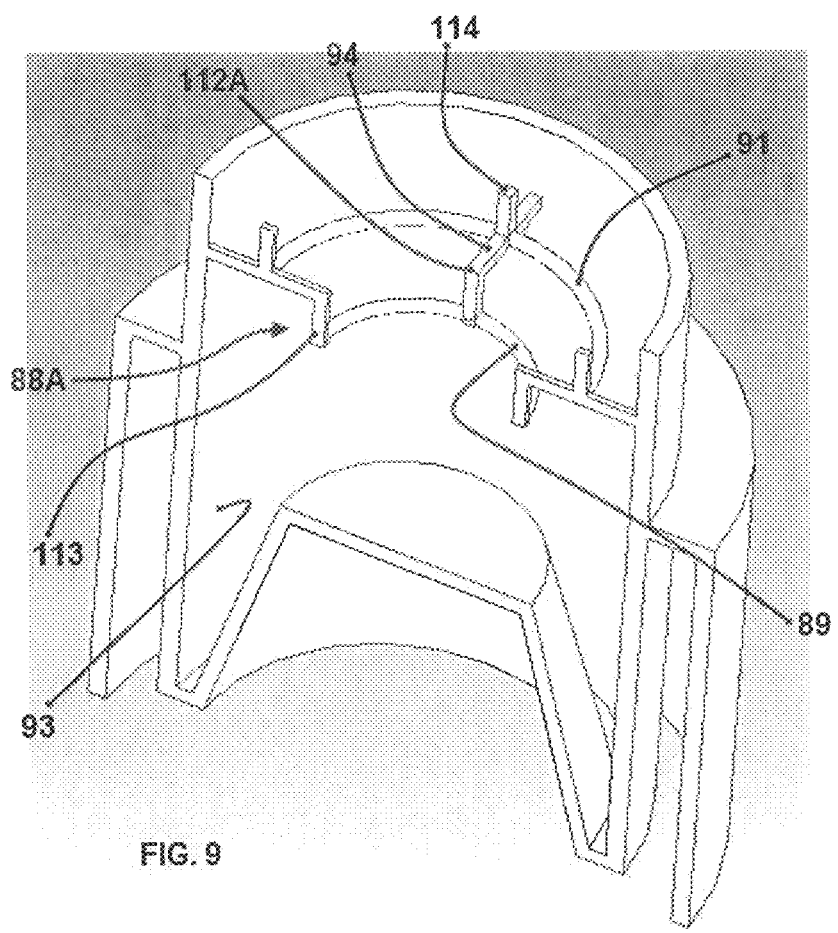
FIG. 9 is a cross sectional perspective view of an illustrative embodiment of an adaptation to the embodiment of FIG. 8A in the event there is concern about the cornea falling past the corneal basket when it is placed into the cornea container. Corneal basket includes optional lower retaining ring and optional upper retaining ring.

To eliminate the possibility of the cornea falling past the corneal basket when it is placed into the cornea container, one or more retaining rings can be added to the corneal basket to prevent that event. FIG. 9 shows an illustrative embodiment of such an adaptation with two retaining rings to demonstrate various options for their location. Corneal basket 88A includes lower retaining ring 89. Lower retaining ring 89 is positioned below disc support surface 112A to avoid continuous contact with a corneoscleral disc and act to prevent a cornea from falling between disc support surfaces 112A. Spars 113 connect retaining ring 89 to disc support surfaces 112A. Although only one spar 113 is needed, three are preferred to provide stability. An alternative and/or second retaining ring location is shown by upper retaining ring 91, which is positioned to prevent the cornea from falling between disc support surfaces 112A (and/or lower ring 89) and container inner sidewall 93. In a preferred arrangement, upper ring 91 resides at or about the diameter of cornea retention posts 114. Regardless of the geometric structure of this embodiment, it is preferred that at least 38%, and more preferably at least 50%, open area exists.

Figure 10A:
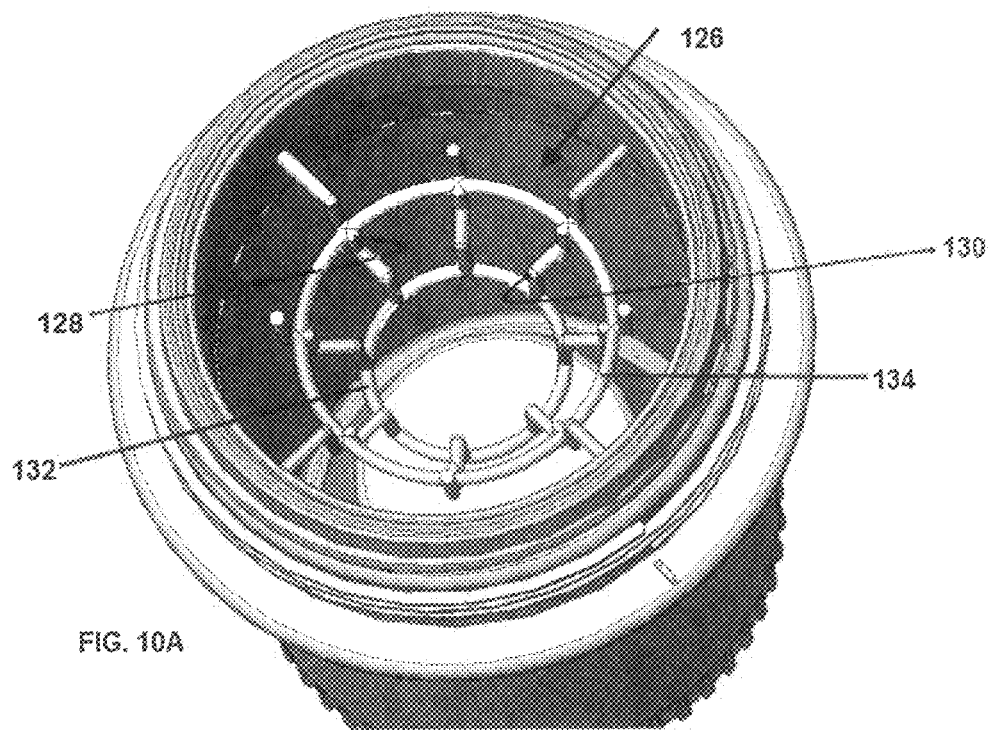
FIG. 10A is perspective view of another embodiment of the present invention with the lid removed for clarity. Corneal basket includes a first disc support surface residing at a height above second disc support surface.
Figure 10B:
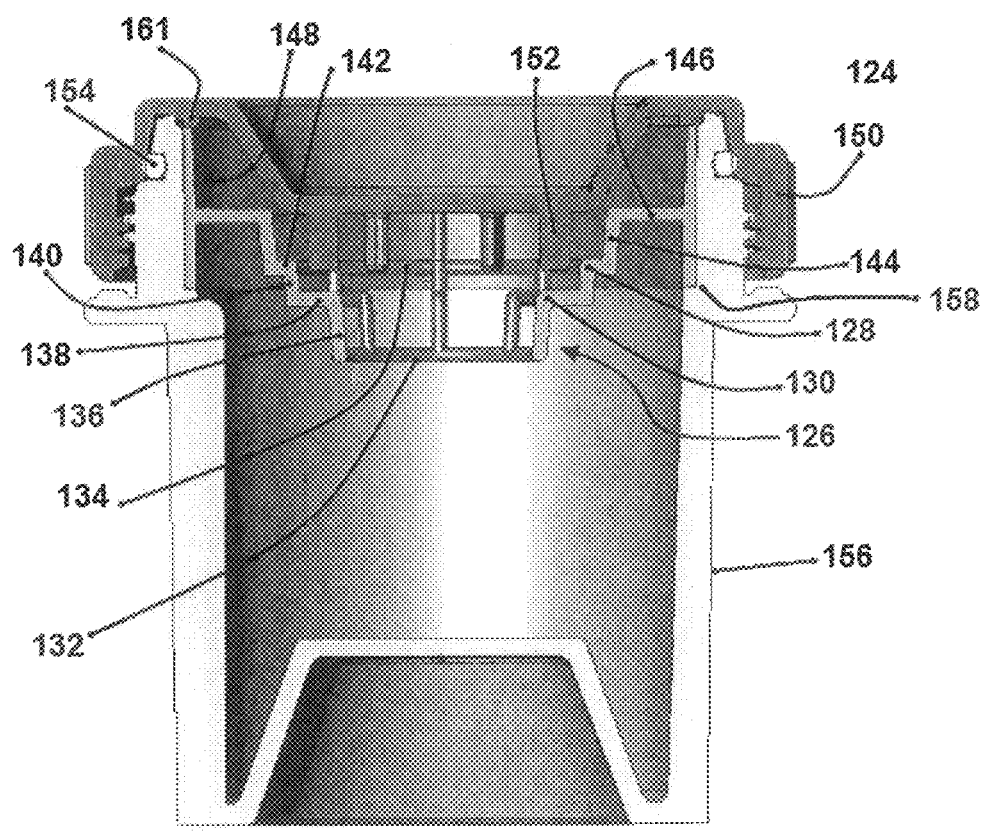
FIG. 10B is a cross sectional view of FIG. 10A with the lid attached.

FIG. 10A and FIG. 10B show an example of an illustrative embodiment of a cornea container that integrates a corneal basket structured to improve preservation medium access to the epithelium while accommodating a wider range of cornea tissue sizes in a manner that exercises superior control over the position of the actual cornea portion of the tissue. In FIG. 10A the lid has been removed to show cornea basket 126. FIG. 10B shows a cross-sectional view with the lid attached. In this depiction, corneal basket 126 includes upper disc support surfaces 128 residing at a height above lower disc support surfaces 130. Upper disc support surfaces 130 act to make contact with larger donor corneas than the donor corneas that will make contact with lower disc support surfaces 130. Although not required, lower retaining ring 132 and/or upper retaining ring 134 can be present to assist the technician in placing the cornea into corneal basket 126. Preferably, upper retaining ring 134 is positioned so that it does not make contact with the corneoscleral disc during transit or storage. Lower spars 136 attach lower retaining ring 132 to lower cornea support rods 138. Lower cornea retention posts 140 mate lower cornea support rods 138 to upper cornea support rods 142. Upper cornea retention posts 144 mate to centering rods 146. Centering rods 146 attach to basket retaining ring 148. Centering rods need not be present at each upper cornea retention post. Thus, some of the upper retention posts can simply terminate without connecting to the basket retaining ring. Lid 150 includes lid projections 152. Lid projections 152 are optional, but preferred to prevent the donor tissue from sticking to lid 152 and to place the corneas at maximum specular microscope focal length for best endothelium access to preservation medium. O-ring 154 makes a liquid tight seal of lid 150 to container base 156. Basket retaining ring 148 is prevented from moving lower by container base shelf 158 and basket retaining ring 148 is prevented from moving upward by lid 150. To prevent medium from getting to o-ring 154, lid seal 161 squeezes corneal basket retaining ring 148 and acts as a redundant seal. Although eight upper and eight lower disc support surfaces are shown, a more preferred embodiment has least three upper and three lower disc support surfaces.

When configuring the embodiment described above and shown in FIG. 10A and FIG. 10B, care should be taken to ensure that basket geometry allows at least 38%, and more preferably at least 50%, open area as determined from the upper disc support surface to the container base to ensure that a large cornea that comes to reside upon the upper disc support surface attains superior solute movement beneath the cornea.

Material selection for any embodiment includes a wide array of materials typically present in any class 1 medical device. Preferably, for lower cost, the parts are injection molded. In the preferred embodiments, the material for the lid and container is clear PET, or any other non cytotoxic material that has relatively similar low carbon dioxide transmission and is not damaged or discolored by gamma irradiation. Low carbon dioxide transmission is beneficial as it acts to minimize pH shifts during storage when the medium includes a sodium bicarbonate buffer. When using an o-ring to create a seal between the lid and container, it is best to select non cytotoxic material compliant with gamma irradiation. Skilled artisans will recognize that there are numerous other options for material selection.

Skilled artisans will recognize that various features of the embodiments illustrated within can be mixed and matched to form a wide variety of configurations that attain the objective of improving cornea health.

EXAMPLES

Example 1

The Effect of Altering Cornea Container Geometry on Corneal Health as Determined by Quantitative Specular Microscope Analysis The aim of quantitative specular microscopic analysis is to assign values to endothelial cells that can provide a measure of their functional status or health of the human cornea. One of the parameters of quantitative specular microscopic analysis is determining the shape of the corneal endothelial cell. In a perfect cornea, endothelial cells demonstrate a perfect 6-sided hexagonal cell. This 6-sided configuration allows for the cell to function optimally. The normal human corneal endothelium is a monolayer of uniformly sized cells with a predominately hexagonal shape. Human corneal endothelial cells that demonstrate great variability in shape or hexagonality are considered to be under physiological stress and abnormal. Corneas that exhibit increased swelling during storage are also considered to be under physiological stress.

Maintenance of corneal deturgescence during corneal storage at 2-8° C. is determined by the barrier function of both the corneal endothelium and the epithelium. The corneal epithelium plays a major role in maintaining a barrier function which prevents the corneal tissue from swelling by preventing fluid into the cornea. Loss of the corneal epithelium during storage greatly increases the swelling of the corneal stroma. Until recently, the importance of the corneal epithelium has not been fully understood. Maintaining all layers of the corneal are equally important and is a goal in optimizing corneal storage at low temperatures.

Increased swelling causes the formation of corneal folds from the thickening of the normal corneal stroma. These folds have a detrimental effect on the corneal endothelium. Increased hydration also increases corneal folds, which contribute to endothelial cell loss. Corneal swelling, if great enough, can also cause cell death to the corneal keratocytes. This increased hydration also causes irregular spacing of the collagen fibrils of the cornea, reducing optical clarity of the cornea. Increased corneal hydration reduces corneal quality, and length of time the cornea can be stored. Therefore, it is of the utmost importance to maintain the corneal epithelium as well as the endothelium.

The functional status of the endothelium and sustained corneal deturgescence during corneal storage are of great clinical importance and contribute primarily to the success of the surgical outcome.

Quantitative specular microscopic analysis of the human corneal endothelium with respect to endothelial cell shape and corneal thickness evaluations were conducted in order to assess the impact of altering viewing container geometry on corneal health.

Cornea containers were constructed in accordance with the present invention as described in the text related to the embodiment depicted in FIG. 10A and FIG. 10B with various dimensions identified in FIG. 11.

Human corneas were stored in identical preservation medium, either in the apparatus of the present invention or Independent Corneal Viewing Chamber™. Corneas were stored at 2-8° C. for 14 days. Pre storage and 14 day post storage central corneal thickness measurements and endothelial cell photographs were obtained for each cornea with a Konan Eyebank KeratoAnalyzer (Konan Medical Corporation, Fair Lawn, N.J.).

Table 1 and Table 2 show a summary of the results.

TABLE 1

HUMAN CORNEAL ENDOTHELIAL CELL HEXAGONALITY
(PERCENT OF HEXAGONAL ENDOTHELIAL CELLS)

| APPARATUS | PRE % Hexogonality | 14 Days % Hexogonality | Percent change in mean hexagonality |
|---|---|---|---|
| Present invention | 61.71 ± 6.74% | 60.27 ± 5.83% | −2.33% |
| Independent Corneal Viewing Chamber™ | 60.55 ± 7.40% | 57.91 ± 6.66% | −4.36% |

The data of TABLE 1 show the ability of the apparatus of the present invention to improve cornea health by demonstrating a 46.56% increase in mean endothelial cell hexagonality as compared to the Independent Corneal Viewing Chamber™ (i.e. −2.33% divided by −4.36%) after 14 days storage at 2-8° C.

TABLE 2

HUMAN CORNEAL THICKNESS EVALUATION

| APPARATUS | PRE μm | 14 Days μm | Percent change in mean corneal thickness |
|---|---|---|---|
| Present invention | 540.80 ± 23.99 | 511.80 ± 21.19 | −5.36% |
| Independent Corneal Viewing Chamber™ | 541.20 ± 26.51 | 518.40 ± 23.32 | −4.21% |

The data of TABLE 2 show the ability of the apparatus of the present invention to improve cornea health by demonstrating a 27.3% decrease in cornea thickness relative to the Independent Corneal Viewing Chamber™ (i.e. −5.36% divided by −4.21%).

Example 2

Figure 12:
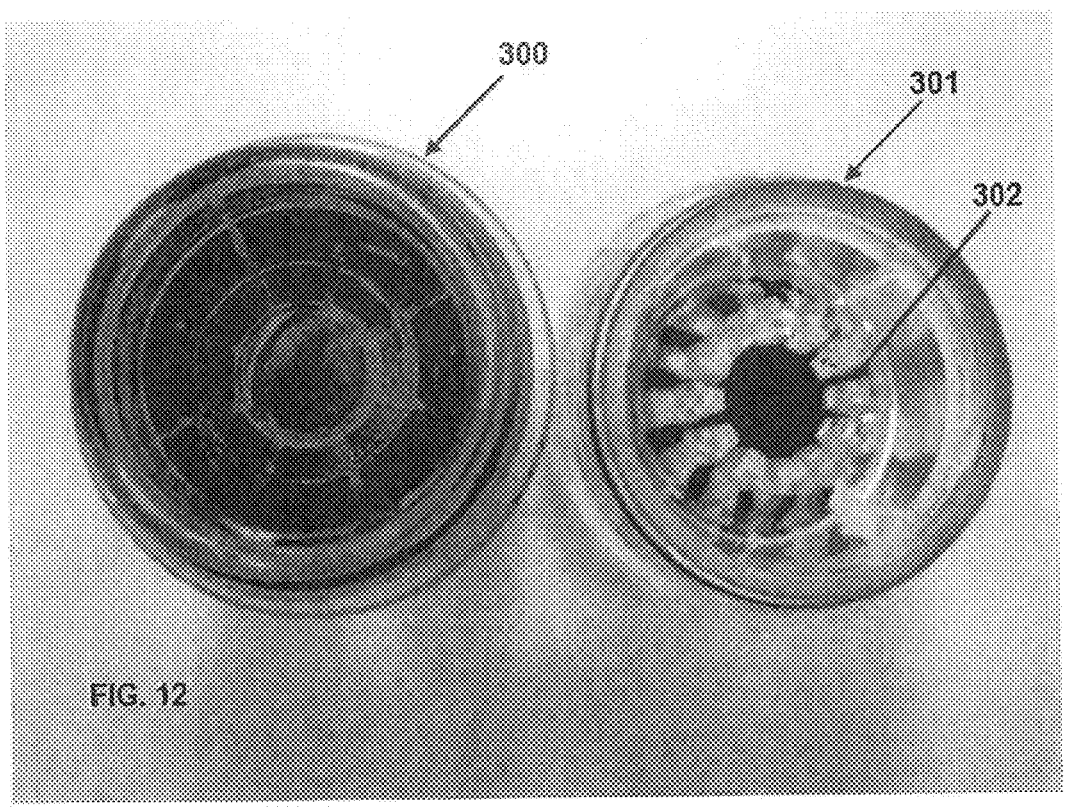
FIG. 12 shows a top view of the devices and results described in Example 2.

The ability for dye to disperse within a cornea container of the present invention, constructed as described in Example 1, was compared to that of an Independent Corneal Viewing Chamber™. Cornea container devices resided upon a stationary surface with their lids removed and the container base of each device was filled with water. Then, trypan blue was dispensed into each device in proximity of the center of corneal basket in the area where the cornea would reside. Photographs were taken. The photograph of FIG. 12 shows a typical example of the pattern of trypan blue dye dispersion in each apparatus. As clearly shown in FIG. 12, trypan blue easily dispersed throughout cornea container 300 (i.e. the apparatus of the present invention). To the contrary, the majority of trypan blue remained trapped in the corneal basket of Independent Corneal Viewing Chamber™ 301, with a relatively small amount moving into the surrounding liquid in a poorly distributed pattern forced by the small gap between prongs 302. This indicates the superior ability of the apparatus of the present invention to distribute solutes to and from the cornea. For example, lactate from the endothelium of corneas in the Independent Corneal Viewing Chamber™ has to overcome the barrier of the traditional corneal basket to dilute into the surrounding medium.

Those skilled in the art will recognize that numerous modifications can be made thereof without departing from the spirit. Therefore, it is not intended to limit the breadth of the invention to the embodiments illustrated and described. Rather, the scope of the invention is to be interpreted by the appended claims and their equivalents.

What is claimed is:

1. A viewing chamber for storing and viewing corneal tissue comprising:
   a container having a container viewing window in a container base and a corneal basket arranged within said container base, said corneal basket in contact with an inner sidewall of the container and adapted to support a corneoscleral disc by including more than one corneal support rod each having a disc support surface; and
   a lid that sealingly engages with said container, said lid including a lid viewing window and said disc support surface is within 0.26 inches from said lid viewing window, and
   each said disc support surfaces is capable of contacting the sclera of a corneoscleral disc without making contact with the cornea of the corneoscleral disc.

2. The viewing chamber of claim 1 further comprising a multi-seal system that includes a threaded seal, said lid and said container having mating threads to sealingly engage each other, and an O-ring seal, said lid having a recess for receiving an O-ring, and a taper seal, said container having an inner wall with a first taper and said lid having an outer wall with a second taper, and wherein, when said lid sealingly engages with said container, said mating threads provide a first seal, said O-ring presses down against an upper edge of said container, so as to provide a second seal, and said second taper is forced against said first taper, so as to form a said taper seal.

3. The viewing chamber of claim 1 further comprising lid projections emanating from the side of the lid opposing the chamber base when said lid is in its sealingly engaged position.

4. The viewing chamber of claim 1 wherein said lid includes a gas trap.

5. The viewing chamber of claim 1 wherein said disc support surface is beyond 0.05 inches from said lid viewing window.

6. The viewing chamber of claim 1 wherein said disc support surface is beyond 0.20 inches from said lid viewing window.

7. The viewing chamber of claim 1 including a plurality of corneal retention posts.

8. The viewing chamber of claim 7 including wherein each corneal retention post is attached to a corneal support rod.

9. The viewing chamber of claim 8 wherein each said disc support surface is an equal distance from said lid viewing window.

10. The viewing chamber of claim 8 wherein each said disc support surface is oriented in a circular pattern at uniform intervals about the corneoscleral disc when the corneoscleral disc resides in said view chamber.

11. The viewing chamber of claim 1 including at least three said disc support surfaces.

12. A method of using the viewing chamber of claim 1 comprising:
   adding media into said container base,
   placing the corneoscleral disc into said corneal basket, said cornea in contact with said media, and
   attaching said lid to said container base.

\* \* \* \* \*